United States Patent [19]

Carlson

[11] 4,301,405
[45] Nov. 17, 1981

[54] INTERVAL-TO-RATE CONVERTER

[75] Inventor: Scott W. Carlson, Blaine, Minn.

[73] Assignee: Cardiac Pacemakers, Inc., St. Paul, Minn.

[21] Appl. No.: 87,790

[22] Filed: Oct. 24, 1979

[51] Int. Cl.$^3$ ............................................. G01R 23/02
[52] U.S. Cl. ................................. 324/78 D; 128/696
[58] Field of Search .................. 324/78 D, 83 D, 163; 128/696, 702, 703, 706; 368/118

[56] References Cited

U.S. PATENT DOCUMENTS 3,928,797  12/1975  Kieneke .............................. 324/78 D
4,020,418  4/1977  Burrage .............................. 324/78 D Primary Examiner—Michael J. Tokar
Attorney, Agent, or Firm—Orrin M. Haugen; Thomas J. Nikolai

[57] ABSTRACT

A pulse interval to pulse rate converter for use in a portable, battery-powered, hand-held test instrument useful for evaluating the performance of a pulse generator such as a cardiac pacer or the like. A pulse generator being tested generates output pulses at an unknown rate and it is desired to measure this rate and to visually display same in units of pulses per minute. A count representative of the interval between successive pulses is developed in a first digital counter and subsequently stored in a holding register, thereby freeing the first counter to continue to measure subsequent pulse-to-pulse intervals. A digital downcounter, arranged to be decremented at a fixed high rate, receives the stored interval value and a tally is developed in a display counter of the number of times that the interval value can be decremented to zero within a known time period, e.g., one second. The count developed in the display counter thus corresponds to the rate value expressed in units of pulses per minute (ppm).

5 Claims, 6 Drawing Figures

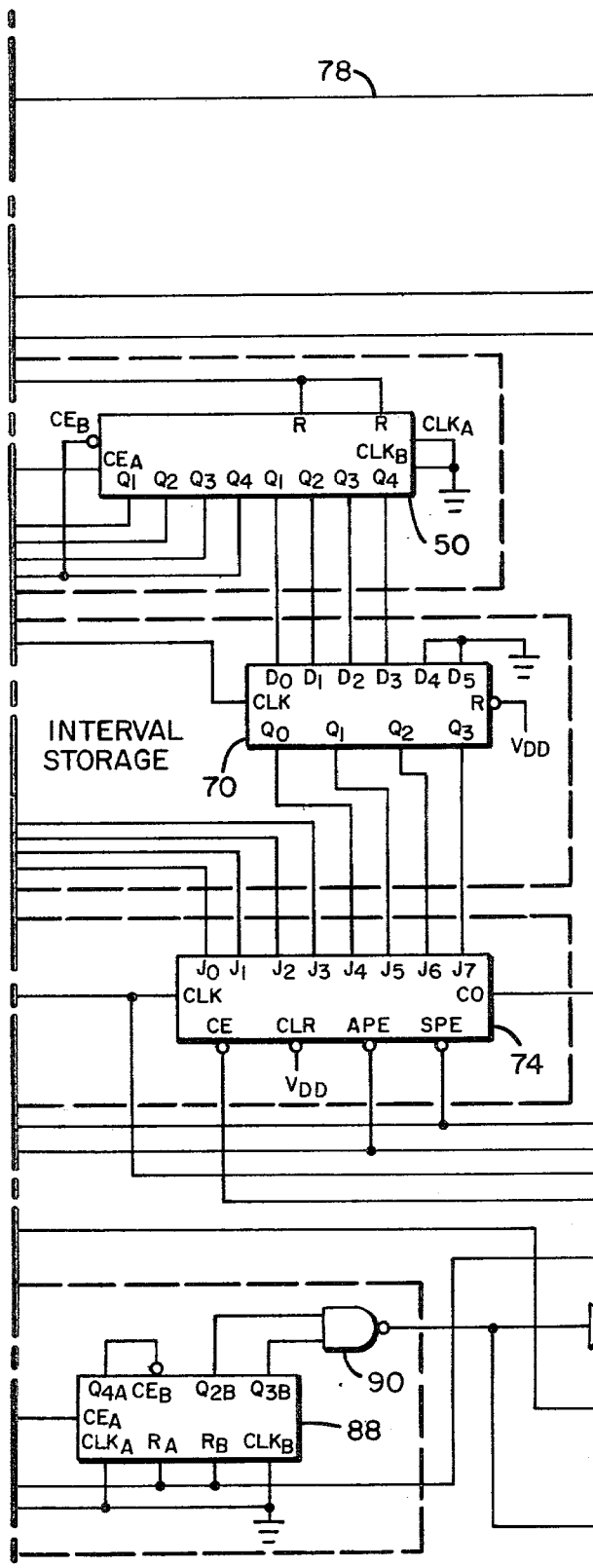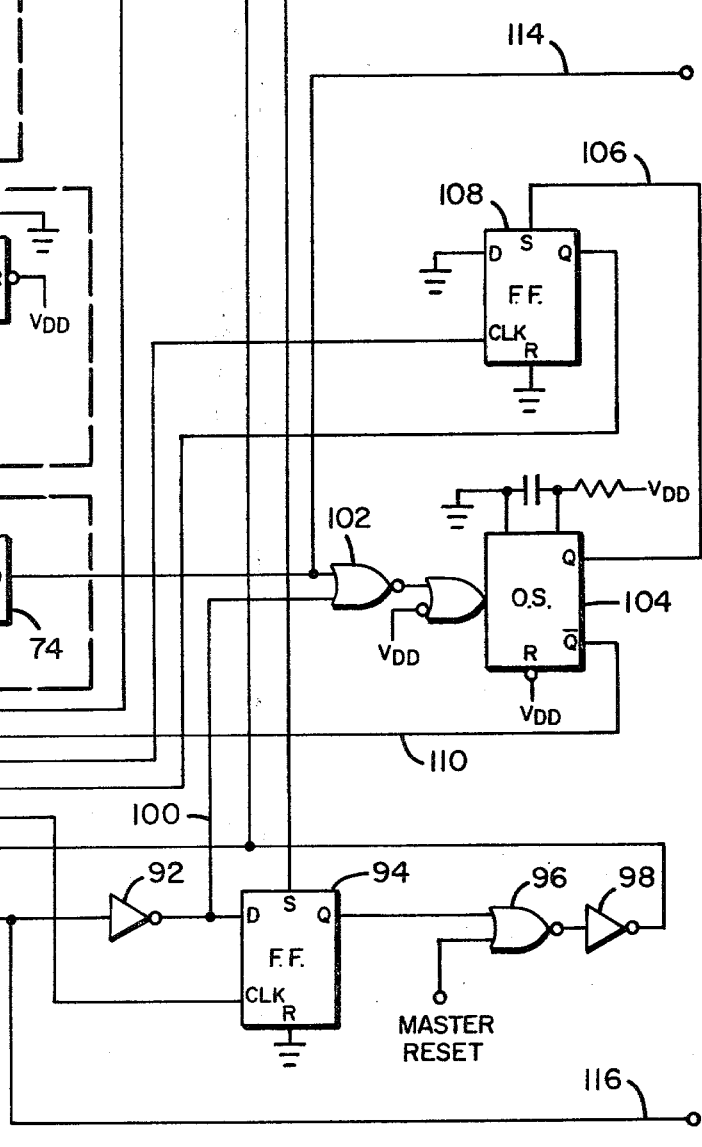
Fig. 4b
Fig. 4

INTERVAL-TO-RATE CONVERTER

BACKGROUND OF THE INVENTION

I. Field of the Invention

This invention relates generally to apparatus for measuring the pulse repetition rate of an electronic circuit, and more specifically to an interval-to-rate converter circuit suited for use in developing, measuring and displaying the repetition rate of the output from a signal generator.

II. Discussion of the Prior Art

To properly evaluate the performance of certain electronic equipment, such as a cardiac pacer, it is desirable to be able to measure the frequency or pulse repetition rate of that device and provide a visual display of that parameter in units of pulses per unit of time. Well known digital counting techniques are available for measuring the time interval between successive pulses. Typically, the leading edge of a first pulse in a sequence may open a gate which allows regularly occurring clock pulses to be entered into a counter. The gate is subsequently closed by the leading edge of the next pulse generator output pulse. The count thus developed in the counter is a measure of the interval between pulses. This interval is expressed in units of time, e.g., seconds or milliseconds. While the interval so measured is directly related to the pulse repetition rate, it is oftentimes desirable to present to a human user a rate reading in terms of pulses per unit of time.

Three different solutions to this problem have been proposed in the prior art. First, and perhaps most trivial, a printed table may be presented which correlates the interval measurement in units of time to a rate value in terms of pulses per unit of time. Typical of this conversion table approach is the Medtronic 5300 tester which includes a printed chart on the back of the device. One using this arrangement must take the interval measurement and then manually look up in the chart or table the rate value corresponding to this interval. This scheme suffers from many drawbacks, not the least of which is the fact that there is not sufficient room on the equipment to list all of the possible intervals and their corresponding rate values. Because the desired interval may not be present, it requires an interpolation with a resultant loss in accuracy. Furthermore, this approach is inconvenient and time consuming.

A second solution for developing a conversion between pulse-to-pulse interval and pulse rate requires the use of a calculator chip which typically requires at least two well regulated power supplies.

Still another possible approach involves the use of a read only memory (ROM) type look-up table. This latter approach suffers from two main drawbacks. First of all, it requires at least ten custom ROM's to obtain sufficient storage which would allow conversion of 3,000 different intervals to their respective rates. This necessarily increases the size of the test instrument and, in addition, is somewhat costly because of the custom nature of the ROM device.

SUMMARY OF THE INVENTION

The present invention obviates the drawbacks of the aforementioned prior art approaches. In accordance with the teaching of the present invention a rate-multiplier configuration is used to solve the equation:

$$\text{Rate (PPM)} = \frac{60,000}{\text{Interval (ms)}}$$

by repeated subtraction. More specifically, regularly occurring clock pulses of a known frequency are applied through a gating circuit to a binary counter during the period between the leading edge of a first external pulse generator pulse and the leading edge of the next such pulse. As such, the counter contents constitute a measure of the interval between the two pulses. Where the clock rate is, for example, 1 KHz, the number entered into the so-called Interval Counter would be expressed in milliseconds. At a time determined by a Conversion Start/Stop control circuit, the contents of the Interval Counter are loaded into a buffer register, thus freeing the Interval Counter so that it may be used to accumulate pulses representative of other intervals as the conversion process performed by the remainder of the circuitry takes place. Again, under control of the Conversion Start/Stop control circuit, the contents of the buffer storage register are loaded into a digital downcounter which is arranged to be decremented at a fixed, known rate. Each time the downcounter reaches zero, an output signal is produced therefrom and used to advance a value contained in the display counter. This same output signal is fed back to the downcounter's "Load" terminal such that the interval value stored in the buffer register is again entered into the downcounter. This process continues repetitively until a timer device indicates that a predetermined time interval has ended. Typically, the timer may be arranged to produce its output when the count entered therein reaches 600,000, the timer being advanced by 600 KHz clock signals. The ending of the time interval also causes a signal to be produced for gating the tally contained within the display counter into a buffer register associated with a LED 7-bar multidigit display panel.

In effect, then, the circuitry thus far described operates to determine how many times the measured interval expressed in milliseconds must be subtracted from 600,000 before the result equals zero. This number constitutes a rate reading in tenths of ppm. For example, if the interval between pulses of the circuit under test is 833 milliseconds, 600,000—Rate (833)=0 implies that the rate equals 720 tenths of a pulse per minute. The display counter employed has the capability to accumulate new data while displaying old data. Hence, the display remains stable as new intervals are being accumulated for later processing.

The converter made in accordance with the present invention has been found to operate over a supply voltage range of from 4.0 to 15.0 volts DC. The supply current required is less than 1 milliampere, excluding the display and display counter requirements. The rate over which the converter will work with a ±1 percent of better accuracy is 10.0 to 600 ppm. The conversion is accurate to within ±0.4 percent from 25 ppm to 240 ppm. This implies that for a rate of 72 ppm, the display will show 71.7 to 72.3 ppm. In addition, only a limited number of integrated circuit parts are required and all are readily available from a number of commercial sources.

OBJECTS

It is accordingly a principle object of the present invention to provide a new and improved conversion apparatus for converting a time interval between successive pulses into a rate reading measured in pulses per unit of time.

Another object of the invention is to provide a interval-to-rate converter which is inexpensive to manufacture, yet highly accurate, so that it may be employed to make precision measurements.

A further object of the invention is to provide an interval-to-rate converter circuit which effectively operates utilizing a repeated subtraction algorithm.

A still further object of the invention is to provide a test instrument of the type described in which the pulse rate of a pulse generator under test may be visually displayed in units of pulses per minute or other units of time.

These and other objects and advantages of the invention will become apparent to those skilled in the art from the following detailed description of a preferred embodiment when considered in conjunction with the accompanying drawings in which like numerals in the several views refer to corresponding parts.

DESCRIPTION OF THE DRAWINGS

FIGS. 4a and 4b, when arranged as in FIG. 4. depict a logic diagram of a preferred implementation of the system depicted diagrammatically in FIG. 2.

DESCRIPTION OF THE PREFERRED EMBODIMENT

Figure 1:
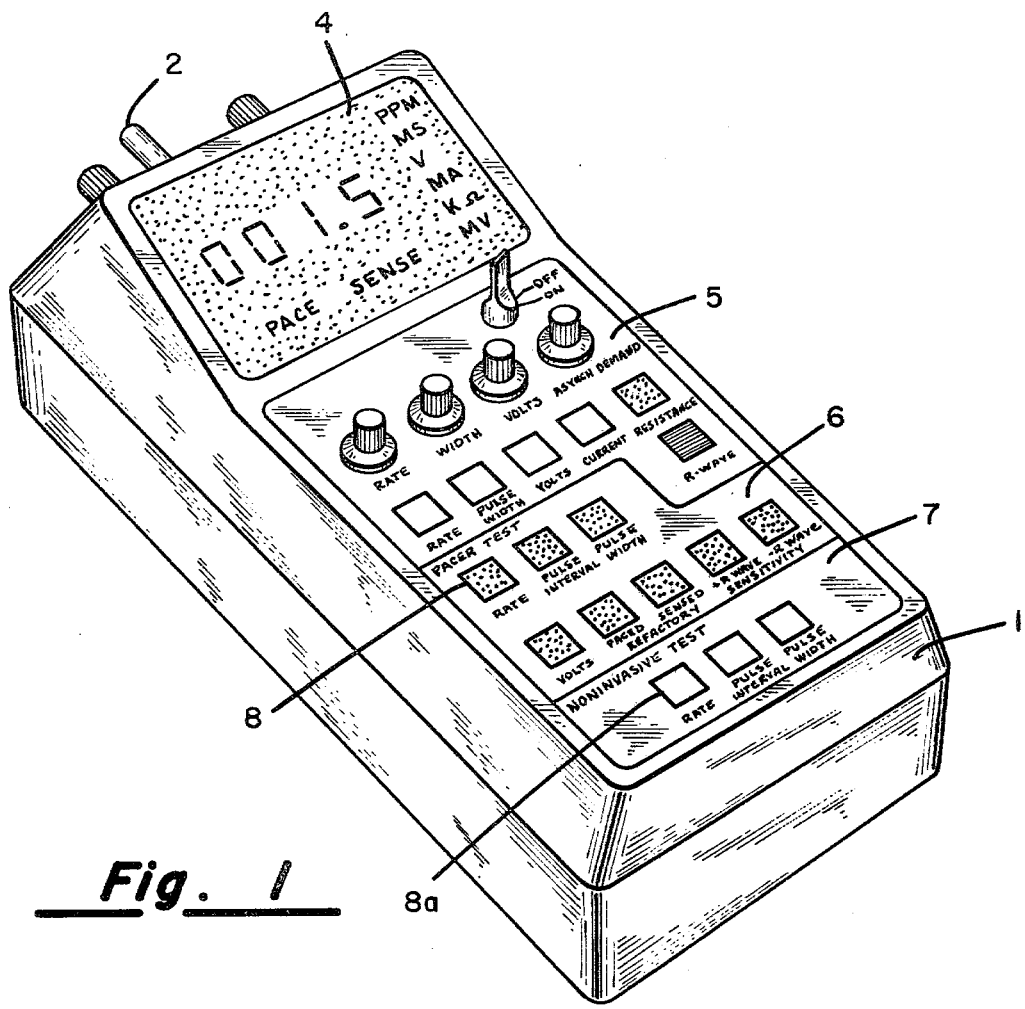
FIG. 1 is a perspective view of the test instrument embodying the invention.

Referring first to FIG. 1, there is shown a perspective view of a portable, hand-held, battery-operated test instrument in which the present invention is incorporated. The device includes a housing 1 which is arranged to contain a plurality of printed circuit boards containing the electronic devices for implementing the present invention as well as various other functions. The housing 1 also contains a battery power supply (not shown). Located at the top end of the housing 1 are a plurality of terminals as at 2–3 to which electrical leads may be connected so that a pulse generator under test may input its output signals to the test instrument.

Referring to the top surface of the instrument when viewed as in FIG. 1, it can be seen that the operator's panel is effectively divided into four segments, namely, a display area 4, a threshold test panel 5, a pacer test panel 6 and a non-invasive test panel 7. Because the present invention is concerned with a circuit for measuring and converting a pulse-to-pulse interval to a rate reading in beats per minute, only the push button 8 labeled "RATE" and the display panel 4 are of interest. When either of these push buttons 8 and 8a are depressed, the internal circuitry to be described operates to develop a visual readout of the rate at which an external pulse generator is developing output pulses, the rate being expressed in units of pulses per minute. With the foregoing general understanding of the nature of the device in mind, consideration will now be given to the particular implementation of the conversion circuitry.

Figure 2:
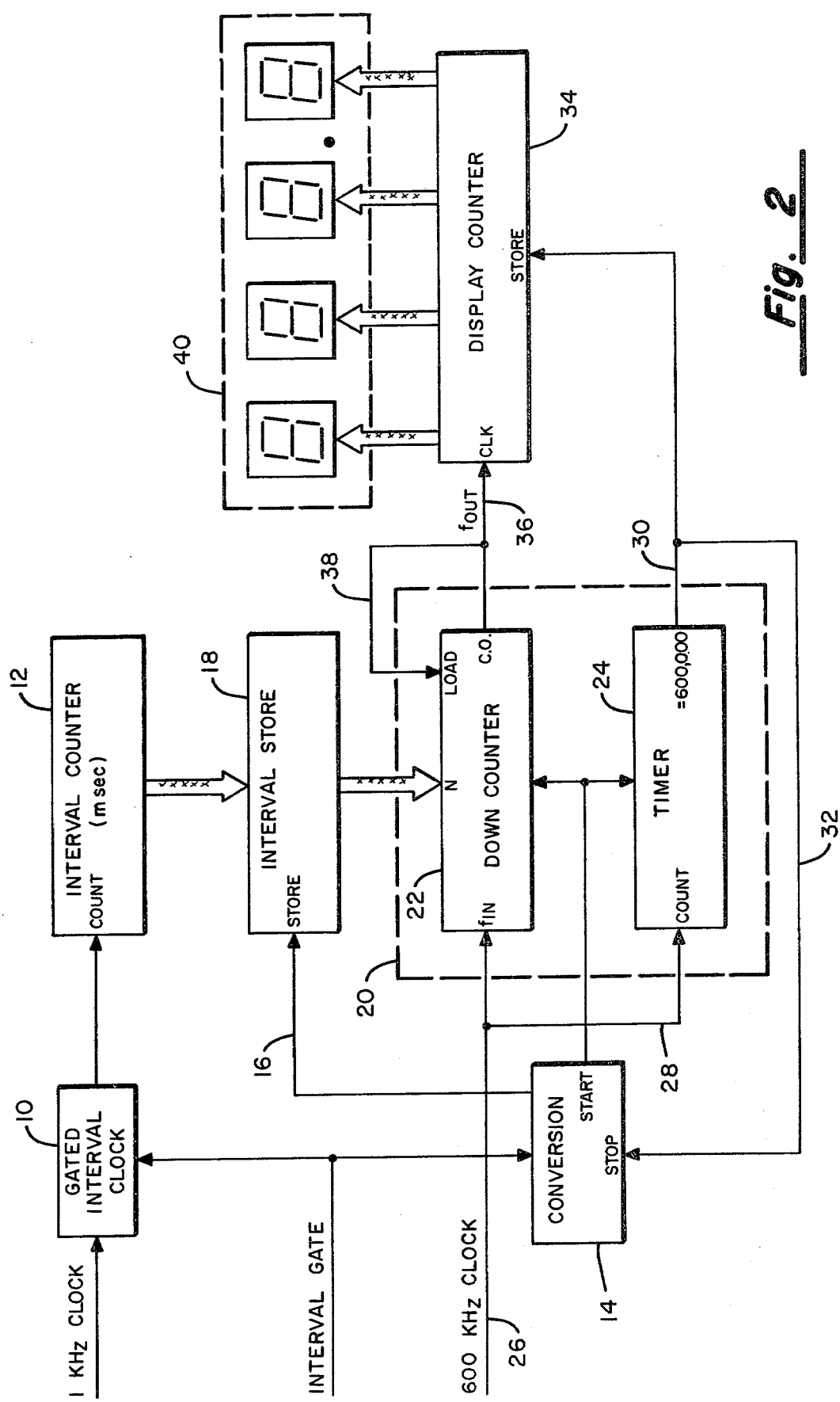
FIG. 2 is a general block diagram illustrating the overall organization of the interval-to-rate converter of the present invention.

Referring now to FIG. 2, a 1 KHz clock source (not shown) feeds regularly occurring clock pulses through the Gated Interval Clock circuit 10 to the Count terminal of an Interval Counter 12. The Gated Interval Clock 10 is arranged to be enabled by the leading edge of a first pulse generated by a pulse generator under test and to be inhibited by the leading edge of a second pulse from that device. Because a 1 KHz clock is employed, the value entered into the Interval Counter 12 represents the time between successive pulses from the unit under test expressed in milliseconds. Under control of a pulse from a Conversion Start/Stop control circuit 14 applied by way of line 16, the interval count contained within the counter 12 may be loaded into the Interval Store circuit 18 where it is held until the rate conversion operation has been completed. Once an interval value has been entered into the storage device 18, the Interval Counter 12 is free to accept further clock pulses via the Gated Interval Clock 10 to measure subsequent interpulse intervals.

The system further comprises a Rate Multiplier shown enclosed by dashed line box 20. Included within the Rate Multiplier are a Presettable Downcounter 22 and a Digital Timer unit 24. The Presettable Downcounter 22 has its inputs connected to the output lines from the Interval Store device 18 and when the load input thereto is stimulated, the contents of the Interval Store are entered into the Downcounter. The counter 22 is arranged to receive regularly occurring clock pulses via line 26 from a clock pulse source which preferably produces output signals at a rate of 600 KHz frequency. These same clock pulses are applied via line 28 to the count terminal of a Digital Timer 24. The counter 24 is arranged to issue an output signal on line 30 whenever the 600,000 value is reached. Such an output control signal is applied via a line 32 to the stop input of the Conversion Start/Stop circuit 14 to end the process. At the same time, the signal on conductor 30 is applied to the store terminal of a Display Counter 34.

The carry overflow terminal (C.O.) of the Presettable Downcounter 22 connects to the clock (CLK) input of the Display Counter 34 such that when the Downcounter reaches zero, a signal is produced on line 36 to increment the Display Counter. This same signal is fed back via line 38 to the "Load" input terminal of the Downcounter 22. As such, the interval value contained within the buffer storage device 18 is repetitively entered into the Downcounter 22 until such time that the Timer unit 24 times out to signal the end of the conversion process. Upon receipt of the store command on line 30, the tally maintained in the Display Counter 34 is latched in an output register (not shown) whereby the value may be displayed in a LED decimal display unit for observation by the user.

That the conversion arrangement thus far described is operable to effect a conversion from a pulse interval measured in milliseconds (or other units) to pulses per minute (or other unit) will now be explained. As was indicated above, the system of the present invention is arranged to solve the equation 600,000−(Rate).(Interval)=0 where the interval is expressed in milliseconds and "Rate" in tenths of pulses per minute (ppm) is the unknown. The system operates to determine how many times the measured interval fits into 600,000 and the result constitutes the desired rate expressed in tenths of pulses per minute because of the clock rates employed. If it is desired to display the rate reading in terms of pulses per minute, then one need only substitute a 60 KHz clock for the 600 KHz clock but in doing so, one loses a degree of resolution in the conversion process.

Figure 3:
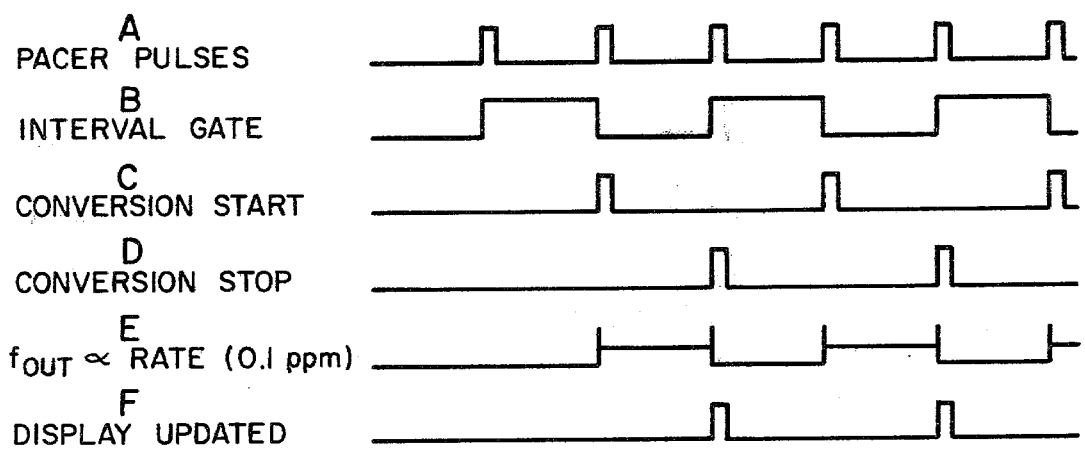
FIG. 3 is a timing diagram helpful in understanding the operation of the system depicted in the block diagram of FIG. 1.

Referring now to the timing diagram of FIG. 3, waveform A represents the pacer pulses of the unit under test. By examining waveforms A and B together, it can be seen that the gate 10 of FIG. 1 is enabled to pass the 1 KHz clock pulses from the leading edge of a first pacer pulse to the leading edge of a next succeeding pacer pulse. Hence, the value entered into the counter 12 is a measure of this pulse-to-pulse interval expressed in milliseconds.

Waveform C illustrates the fact that the conversion process is initiated at the conclusion of the period in which the interval gate is enabled. In a similar fashion, waveform D illustrates that the conversion process terminates when the timer 24 reaches the 600,000 count value upon being incremented by the 600 KHz clock connected to the line 26 in FIG. 2.

During the conversion phase, i.e., between the leading edge of a pulse in waveform C and the leading edge of a pulse in waveform D, the presettable Downcounter 22 develops a pulse train on the line 36 whose frequency is proportional to the desired rate measured in 0.1 ppm. Finally, waveform F illustrates the fact that the Display Counter 34 is strobed by the output from the Timer 24 appearing on line 30 to transfer the digital count entered therein during the conversion phase into a holding register such that a visual display thereof may be presented. Once this transfer has been accomplished, the Display Counter is again free to accumulate pulses during a new conversion cycle while the data from the previous cycle is being displayed. With the clock rates indicated in FIG. 2, the total time from when the interval changes to the time that a new rate is displayed is only 1 second plus a maximum of two conversion intervals. Hence, for a rate of 72 ppm, this corresponds to a 2.67 second response time for the measurement.

Figure 4A:
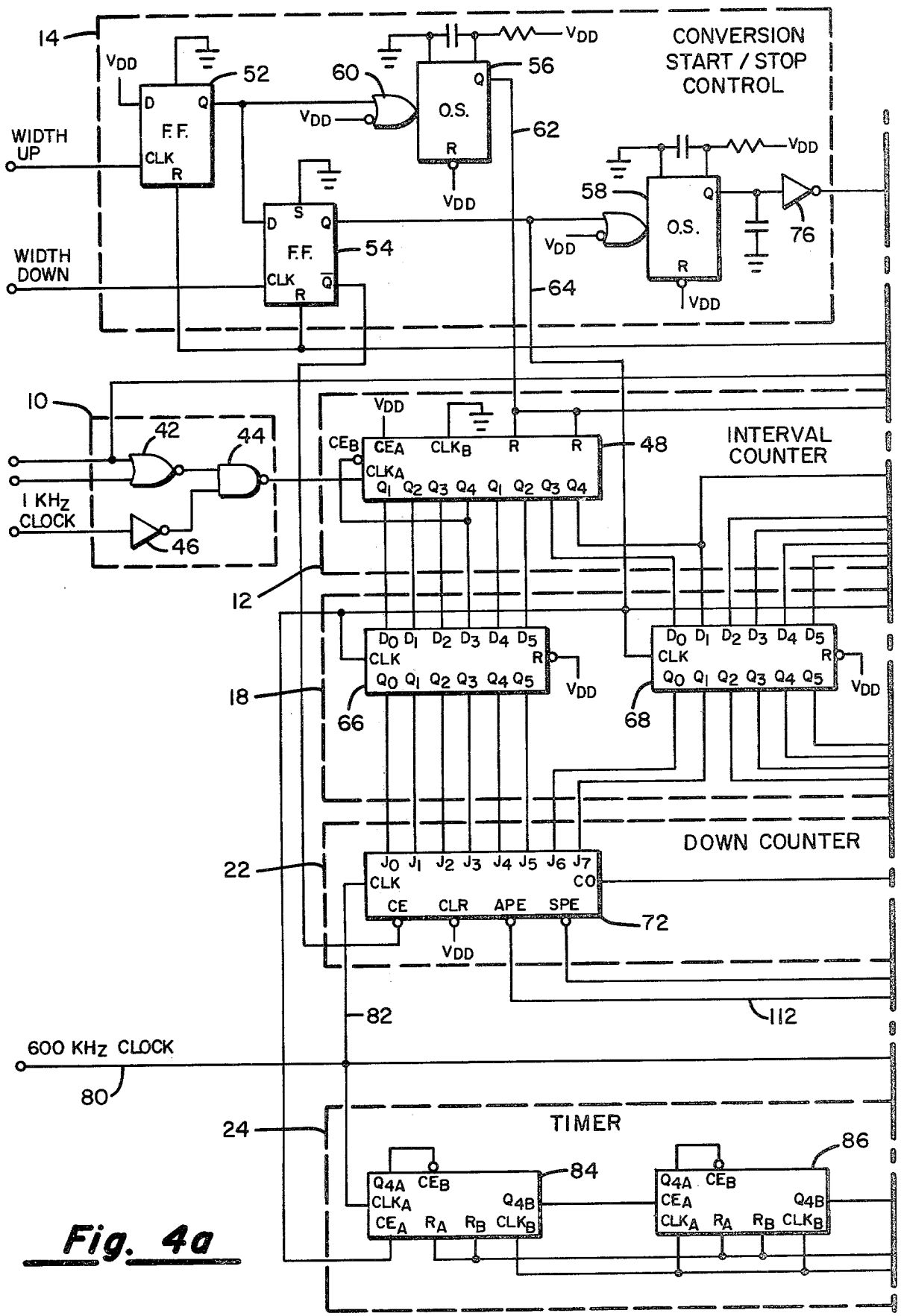

Having described, in functional terms, the overall organization of the preferred embodiment, consideration will now be given to the specifics of the logic implementation and, in this regard, reference will be made to the logic diagram of FIGS. 4a and 4b.

The Gated Interval Clock 10 of FIG. 2 includes a two input NOR gate 42 whose output is connected directly to a first input of a NAND gate 44. The second input to this last-mentioned gate comes from an oscillator or other source of regularly occurring clock signals (not shown) capable of producing output pulses at a rate of 1 KHz by way of an inverter 46. The inputs to NOR gate 42 arrive from logic circuits (not shown) which receive the output from the pulse generator under test and define the period between leading edges of successive input pulses from the generator under test. As such, during a test interval, NAND gate 44 will be fully enabled to allow the 1 KHz clock pulses to propagate to the interval counter 12 comprised of two cascaded integrated circuit dual BCD up-counters. Each consists of two identical, internally synchronous, 4-stage counters, each stage being a D-type flip-flop with interchangeable clock and enable lines for allowing incrementation on either positive-going or negative-going transitions. As such, the composite Interval Counter 12 may store four binary coded decimal digits. With no limitation intended, it has been found that RCA Type CD 4518 B integrated circuits are well suited for the particular application.

The Conversion Start/Stop circuit 14 comprises a pair of D-type flip-flops 52 and 54 and a pair of one-shot circuits 56 and 58. Flip-flop 52 is arranged to be clocked by a leading edge of a first pacer pulse and the Q output therefrom is applied to the one-shot circuit 56 via its OR input 60. The Q output from the flip-flop 52 is also applied to the data, D, input of the flip-flop 54. The clock input for flip-flop 54 comprises a "Width Down" pulse which occurs at the leading edge of the next successive pulse generator output, following that which clocked the first flip-flop 52.

The Q output from the one-shot circuit 56 is connected by a conductor 62 to the reset terminals of the integrated circuit counter chips 48 and 50. Hence, the interval counter 12 is initialized by the occurrence of a leading edge of a first pulse generator output signal.

At this point, then, the 1 KHz clock signals pass through the Gated Interval Clock circuitry 10 and begin incrementing the Interval Counter 12. This action continues until such time that the flip-flop 54 is set which results in a control pulse on the conductor 64 which connects to the CLK inputs of a plurality of integrated circuit D-type flip-flops identified by numerals 66, 68 and 70. Each of these integrated circuits may comprise six identical D-type flip-flops having independent data inputs labeled $D_0$ through $D_5$. These circuits are arranged such that data is transferred to the Q outputs ($Q_0$ through $Q_5$) on the positive-going transition of the clock pulse on conductor 64. Again, with no limitation intended, it has been found that RCA CD 40174 Hex "D"-type flip-flops are well suited for the intended function.

The circuitry thus far described, then, functions to define the interval between two successive input pulses by accumulating regularly ocurring clock pulses in the counter 12 at the onset of the pulse-to-pulse interval and by terminating the accumulation of the regularly occurring clock pulses at the conclusion of that interval. Simultaneous with the conclusion of the interval in question, the Interval Storage device 18 is clocked to accent the transfer of the interval value developed in the Interval Counter 12 and hold this value for subsequent processing. When the one-shot circuit 56 is next triggered a pulse is again developed on conductor 62 for resetting the Interval Counter, making it available to accept clock pulses which will ultimately define a subsequent pulse-to-pulse interval.

The outputs from the interval storage 18 are connected to the jam inputs, $J_0$ through $J_7$ of the counter chips 72 and 74 which, together, comprise the Downcounter 22 of FIG. 1. The integrated circuits 72 and 74 are preferably RCA CD 40102 B 8-stage presettable synchronous downcounters, each capable of storing two 4-bit BCD values. As is indicated in the logic diagram of FIG. 4a, the setting of the flip-flop 54 by the leading edge of the second in a series of received pulses triggers the one-shot circuit 58 and a synchronous preload enable signal (SPE) is thereby applied via inverter 76 and conductor 78 to the SPE inputs of the downcounter chips 72 and 74. This causes the contents of the Interval Storage Register 18 to be entered into the Downcounter 22 as an initial value. A source of clock signals having a 600 KHz frequency (not shown) provides its output on the conductor 80 which connects to the CLK input of the counter chip 72 by way of a conductor 82 and at the same time these 600 KHz clock signals are applied as an input to the Timer circuit 24 comprised of the individual dualup-counter chips 84,86 and 88. Thus, at the same time that the contents of the Downcounter 22 are being decremented, the Timer 24 is being incremented and at the same rate. The chips 84, 86 and 88 may also comprise RCA type CD-4518 up-counters, and, as such, each IC chip stores two BCD digits. The highest order stage output of the counter chip 84 is connected as a clock enable signal (CE) to the counter chip 86. The same thing holds true for chips 86 and 88. The output from stages $Q_{2B}$ and $Q_{3B}$ are connected as inputs to a NAND gate 90. Hence, this last-mentioned gate is satisfied when the count developed within the Timer 24 reaches 600,000. The output from NAND gate 90 is coupled through an inverter 92 to the D input of a D-type flip-flop 94 whose CLK input receives the 600 KHz clock signals from a clock source (not shown). Hence, on the next succeeding clock signal following the time that the counter 24 reaches 600,000, the flip-flop 94 will be set and will output a logical "1" signal to a NOR gate 96 whose output is inverted at 98 and used to reset the flip-flops 52 and 54 of the Conversion Start/Stop circuit 14, as well as the counter chips comprising the Timer 24. It is also to be noted that the output from inverter 92 is applied by way of a conductor 100 to a first input of NOR circuit 102. The output from this circuit is used to stimulate a one-shot circuit 104. The Q output from one-shot 103 is connected by way of a conductor 106 to the set terminal of a flip-flop 108. Flip-flop 108 permits the downcounter chip 74 to respond to the carry output (C.O.) from the counter chip 72 as opposed to a count of zero.

When the downcounter 74 produces a carry output pulse upon reaching zero, the one-shot circuit 104 outputs a signal at its Q terminal which is applied by way of conductors 110 and 112 to the asynchronous preload enable (APE) input terminals of the counter chips 72 and 74. As such, the value contained in the interval storage register 18 is again reloaded into the downcounter and decremented by the 600 KHz clock signals. This process continues until the NAND gate 90 is satisfied by decoding a 600,000 count. As was already mentioned, this event results in the inverter 98 outputting a signal which is fed back to the control flip-flops 52 and 54 in Conversion Start/Stop circuitry 14 to terminate to conversion process.

It can be seen then that the 600 KHz clock is applied to the downcounters 72 and 74 as well as to the timer counters 84, 86 and 88. As soon as that clock is applied to these counters, they begin to count down and after the contents have been counted down, a signal appears at the (C.O.) output of the counter 74 which operates through the logic circuitry already described to re-initiate or repeat the process. It keeps repeating this process until a count of 600,000 is reached in the Timer unit 24. This satisfies the gate 90 and results in a termination of the conversion operation. Meanwhile, all of the carry outputs from the downcounter chip 74 are fed into a Display Counter which accumulates these pulses. The display counter, itself, is not shown in the logic diagram of FIG. 3. Those desiring to have a specific description of the Display Counter and its mode of interconnection to the LED display circuitry are referred to the copending application of James Bartelt, Ser. No. 87,867 filed Oct. 24, 1979 and entitled CARDIAC PACER TESTING SYSTEM, which application is assigned to the assignee of the present invention.

The signal appearing on conductor 114 is used to advance the Display Counter which is described in detail in the aforereferenced Bartelt application. Similarly, the signal appearing at the output of NAND gate 90 when the Timer 24 times out is applied by the conductor 116 to cause the contents of the Display Counter to be transferred into a buffer register which is then used to display the information. When the Conversion Start/Stop logic detects the fact that a new count is available in the Interval Counter 12, the conversion process described above is repeated. This time, as new counts are entered into the display register via conductor 114, the dadta from the previous conversion cycle remains stored in the output register of that display counter. Hence, the earlier reading is continuously displayed until the completion of second cycle of conversion, at which time the new data accumulated in the display counter are written over the previous data contained in the display output register.

The Conversion Start/Stop control circuitry 14 ensures that a complete interval between the occurrence of a width up-pulse and a width down pulse is used as the basis for the interval to be converted. That is, it precludes an initiation of the conversion process when the Interval Counter 12 is only partially loaded and thereby prevents false readings.

The invention has been described with respect to various illustrations and embodiments thereof and also with respect to a drawing of the most preferred embodiment. However, the invention is not to be limited to these because it is evident that one skilled in the art with the present specification, including the drawing and claims, before him, will be able to utilize various substitutes and equivalents without departing from the scope of the invention.

What is claimed is:

1. Apparatus for measuring the repetition rate of pulses in a pulse train of unknown frequency, comprising:
    (a) interval measuring means for developing a binary coded value proportional to the time interval between two successive pulses in said pulse train;
    (b) first means connected to periodically receive said binary coded value from said interval measuring means;
    (c) second means for establishing a known time period;
    (d) control means connected to said first means for repeatedly decrementing said binary coded value to zero and re-entering said binary coded value into said first means when said value reaches zero; and
    (e) third means for tallying the number of times said digital value is decremented to zero during said known time period.

2. Apparatus as in claim 1 and further including display means coupled to said third means for presenting a visual readout of said tally following the expiration of said known time period.

3. Apparatus as in claim 1 wherein said interval measuring means comprises:
    (a) a source of regularly occurring clock pulses of a known frequency;
    (b) gating means connected to receive said clock pulses, said gating means being enabled from the onset of a first of said successive pulses in said pulse train to the onset of the next successive one of said pulses in said pulse train; and
    (c) interval counter means connected to the output of said gating means for accumulating a count of said clock pulses occurring during the interval that said gating means is enabled.

4. Apparatus as in claim 3 and further including an interval storage register connected between said interval counter and said first means.

5. Apparatus as in claim 1 wherein said first means comprises a digital downcounter having a plurality of inputs connected to receive signals originating at said interval measuring means, and a source of regularly occurring clock pulses of known frequency coupled to said downcounter for decrementing the value stored therein to zero at a predetermined rate.

* * * * *